United States Patent [19]
Samuels

[11] Patent Number: 6,159,230
[45] Date of Patent: *Dec. 12, 2000

[54] EXPANDABLE LUMEN DEVICE AND METHOD OF USE

[76] Inventor: Shaun L. W. Samuels, 1055 Sonoma Ave., Menlo Park, Calif. 94025

[*] Notice: This patent is subject to a terminal disclaimer.

[21] Appl. No.: 09/322,829

[22] Filed: May 28, 1999

Related U.S. Application Data

[63] Continuation-in-part of application No. 08/956,951, Oct. 23, 1997, Pat. No. 5,908,435.

[51] Int. Cl.$^7$ .................................................... A61M 29/00
[52] U.S. Cl. .............................................................. 606/200
[58] Field of Search ..................... 606/200, 194, 606/198, 127, 128; 128/898

[56] References Cited

U.S. PATENT DOCUMENTS

| | | |
|---|---|---|
| 5,190,561 | 3/1993 | Graber ..................................... 606/127 |
| 5,549,626 | 8/1996 | Miller et al. . |
| 5,707,359 | 1/1998 | Bufalini . |
| 5,947,995 | 9/1999 | Samuels ................................... 606/200 |

*Primary Examiner*—Michael Buiz
*Assistant Examiner*—Kevin Truong
*Attorney, Agent, or Firm*—Piper Marbury Rudnik & Wolfe

[57] ABSTRACT

A device for removing undesirable material from a tubular structure within the human body features a cylindrical body with a lumen therethrough. The distal portion of the body is divided into a number of flexible members. An inflatable cuff is attached to the flexible members. When the cuff is inflated, the members flex radially outwardly so that the distal opening of the lumen is expanded. An inflation tube is used to inflate and deflate the cuff by means of a syringe. An elastomeric membrane sleeve surrounds the flexible members so that the latter are contracted towards their original position when the cuff is deflated. The sleeve also prevents material from escaping between the flexible members when the cuff is inflated.

24 Claims, 4 Drawing Sheets

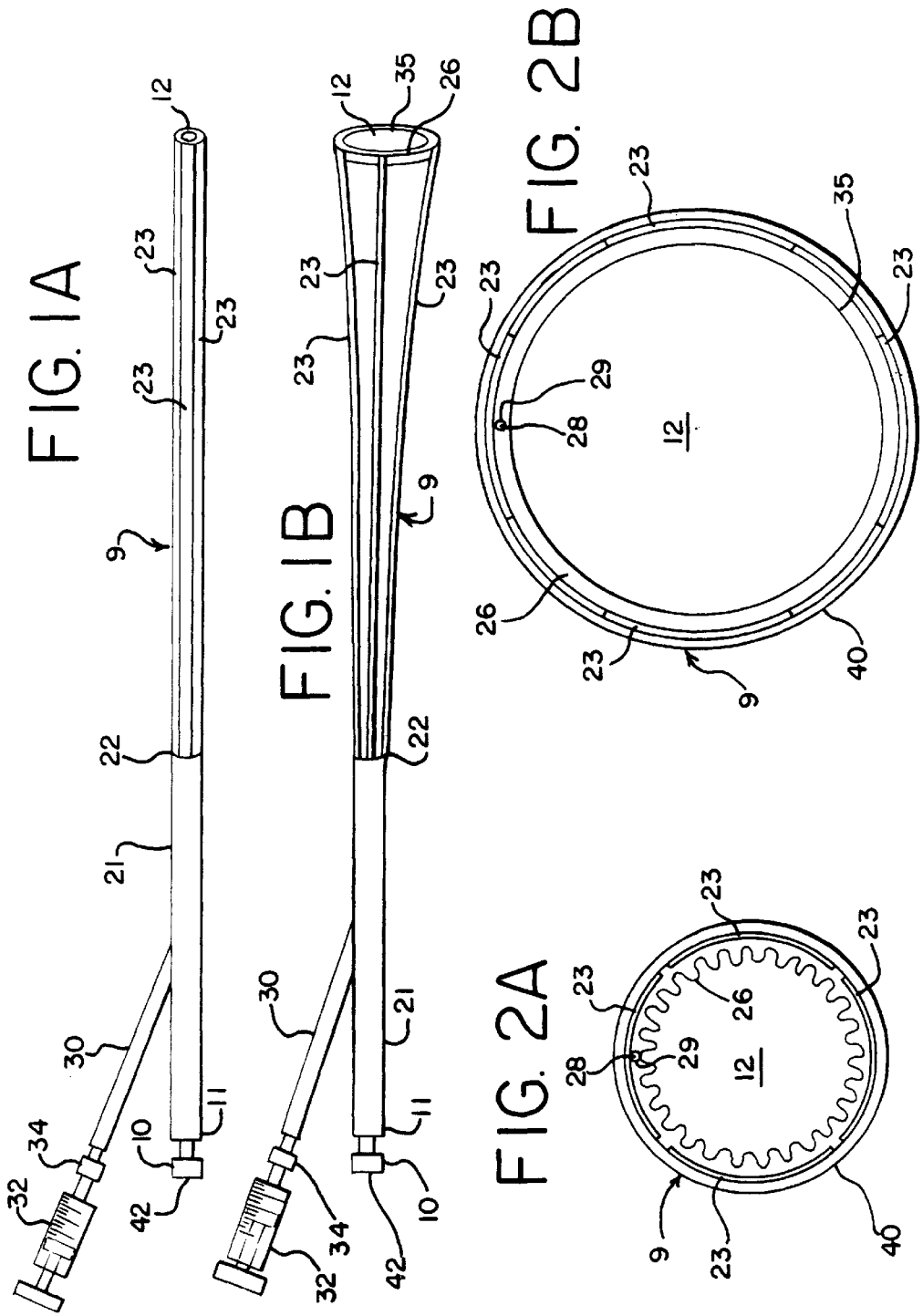

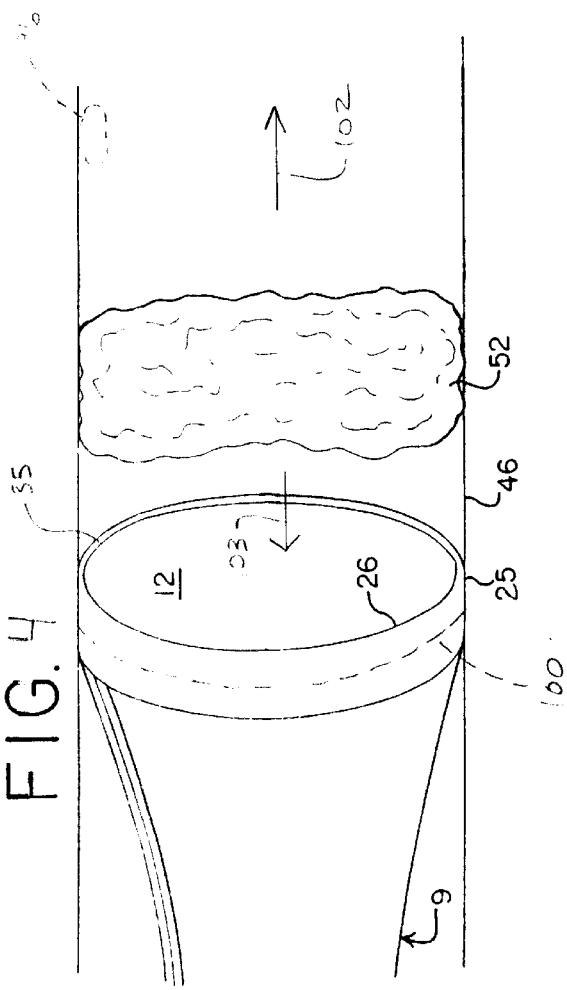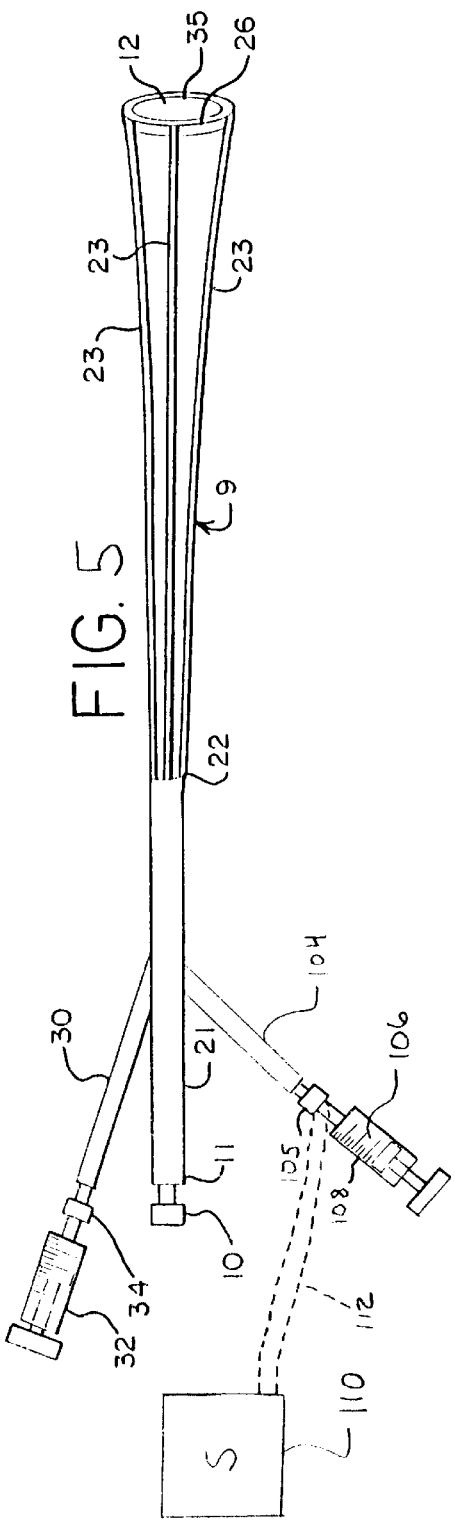

EXPANDABLE LUMEN DEVICE AND METHOD OF USE

CROSS REFERENCE TO RELATED APPLICATIONS

This application is a continuation-in-part of U.S. application Ser. No. 08/956,951 filed Oct. 23, 1997 now U.S. Pat. No. 5,908,435.

BACKGROUND

Various tubular structures within the human body may come to contain materials, whether of the body's origin or man-made, that are undesirable. For example, stones may develop in the biliary or excretory systems, blood clots may form in blood vessels, or surgically implanted devices, such as catheters, may have fragments break off. For most of these situations, surgical intervention has traditionally been the primary means of retrieval and treatment.

Recently, however, various interventional radiological techniques have been developed which allow removal of such undesirable material. Such techniques involve the introduction of guide wires and catheters, or other medical devices, into the lumen of the tubular structures through introducer sheaths.

In one type of interventional radiological technique, various baskets, such as the SEGURA basket, manufactured by the Meditech company of Watertown, Mass., are used for trapping stones in the biliary and excretory tracts. Unfortunately, such devices are not easily inserted into, or manipulated within, the lumen of a human body's tubular structures. The baskets also generally contain wire mesh that may damage the interior walls of tubular structures.

Interventional radiologic techniques have been developed in which pharmacologic agents, such as urokinase, are used through catheter directed infusion to dissolve blood clots. This dissolving of clots is a relatively lengthy process and is extremely expensive. Furthermore, the process poses significant risks to the patient, the most serious of these being the precipitation of bleeding elsewhere in the body.

In U.S. Pat. No. 4,927,426 to Dretler, there is disclosed a device for capturing and disintegrating kidney stones and the like. The device features a snare that passes through the lumen of a catheter. Once the catheter is positioned within a passage of the human body, such as the urinary tract, the snare may be extended out of the catheter's distal end in an axial direction so that it may capture a kidney stone. The catheter has an elastomeric structure on its distal end which is inverted on itself as the kidney stone is drawn axially into the lumen of the catheter. The snare features an elongated tube through which a laser fiber passes. This allows the kidney stone to be disintegrated as it is held within the catheter. A disadvantage of this device, however, is that it features a profile that would preclude introduction into the vascular system. Furthermore, the elastomeric structure on the distal end of the catheter has undesirable consequences, as will be discussed below.

U.S. Pat. No. 5,092,839 to Kipperman discloses a method and apparatus for removing thrombus and plaque from a coronary artery. The apparatus features a balloon catheter disposed through the lumen of a guide catheter. The guide catheter features an expandable distal tip. Once the device is positioned within the artery, the balloon is inflated to expand the distal tip of the guide catheter. The balloon is then deflated and the distal tip of the guide catheter retains its expanded shape. The balloon catheter is then extended out from the distal tip and beyond the occluded portion of the artery and is once again inflated. The inflated balloon is then retracted back into the guide catheter, carrying with it residual pieces of thrombus and/or plaque which had been dislodged from the artery wall. A disadvantage of this apparatus and method, however, is that, in order to properly expand the distal tip of the guide catheter, the balloon must be precisely positioned. Furthermore, once the distal tip is expanded, it cannot be contracted. This would make removal from the patient's body or advancement further into the artery difficult if not impossible.

In order to accommodate the retrieval and removal of foreign bodies that are larger than the inner diameter of their distal tips, a number of sheaths and catheters have been constructed from elastomeric substances. An example is the EVC catheter available from the Applied Medical corporation of Laguna Beach, Calif. A disadvantage of existing elastomeric sheaths and catheters, however, is that, because of their elastomeric construction, they are easily deformed in an accordion-like fashion when an object is brought up forcefully against their orifices. Furthermore, due to their deformability, such sheaths and catheters may be peeled back during introduction through the skin or while entering the target structure. This could render the device useless and may possibly result in damage to the skin or target structure.

Accordingly, it is an object of the present invention to provide a catheter, which may be in the form of a typical catheter, a guide catheter or an introducer sheath, and a method of use by which a variety of undesirable materials may be removed from tubular structures within the human body.

It is also an object of the present invention to provide a catheter with a lumen which may be easily expanded once the catheter is introduced into a tubular structure of the human body so as to allow for passage of materials into the tip of the catheter for easier removal from the body.

It is a further object of the present invention to provide a catheter with an expandable lumen that is elastic so that it may be contracted back to its original size while in a tubular structure in the human body.

It is a further object of the present invention to provide a catheter which allows for elastic expansion of its lumen while maintaining adequate longitudinal strength to resist accordion-like deformation.

It is still a further object of the present invention to provide a catheter which allows for elastic expansion of its lumen and may be easily introduced and withdrawn from a tubular structure of the human body.

SUMMARY

The present invention is directed to an expandable lumen device for retrieving material from tubular structures within the human body. The device is particularly useful for retrieving material that normally would be too large for the opening of a typical catheter or sheath. The device may take the form of a catheter, sheath or the like. It features a cylindrical body defining a central lumen with a distal opening. The proximal portion of the body features a solid wall while the wall of the distal portion is divided into a plurality of flexible members.

An inflatable cuff is attached to the interior surfaces of the flexible members near the distal opening of the lumen. As a result, when the cuff is inflated, the flexible members move radially outwardly so as to expand the distal opening of the lumen so that relatively large materials may be retrieved into the lumen. An elastic sleeve surrounds the flexible members so that they are drawn together when the cuff is deflated. The elastic sleeve also prevents the escape of material between the flexible members when the cuff is inflated.

A cuff inflation tube is in fluid communication with the inflatable cuff and is secured to the interior surface of one of the flexible members and runs longitudinally through the central lumen. The proximal end of the cuff inflation tube is in communication with a side port which in turn is in communication with a syringe. Manipulation of the syringe causes the cuff to inflate.

In use, a guide wire is introduced into a tubular structure of the human body. Next, the device, with a central dilator in its lumen, is guided via the guide wire through the tubular structure to the location of the material to be removed. Once the device is in position, the central dilator is removed. The cuff is then inflated so as to enlarge the distal opening of the lumen to a size that is compatible with the material. A balloon catheter, snare or other elongated tool is then fed through the lumen and is used to push or pull the material into the central lumen of the device. The retrieving apparatus may alternatively be inserted into the tubular structure through a second puncture site downstream of the material. Once the material is captured within the device, the cuff is deflated so that the distal opening of the lumen contracts. The material may then be removed from the tubular structure through the central lumen or the entire device itself may be removed with the material captured inside.

The distal lumen opening and cuff may be sized so that the distal tip of the device forms a circumferential occlusive seal with the inner surface of the tubular structure when the cuff is inflated. This causes a decreased pressure at the entrance to the distal lumen opening and a reversed fluid flow in the tubular structure which, in some instances, is sufficient to carry the material into the device. The physician may apply suction to the proximal end of the lumen to enhance this effect.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIGS. 1A and 1B show perspective views of a catheter that is an embodiment of the present invention with its elastomeric membrane sleeve removed and its cuff in deflated and inflated states, respectively;

FIGS. 2A and 2B show end axial views of the distal end of the catheter of FIGS. 1A and 1B, respectively, with the elastomeric membrane sleeve installed;

FIG. 4 shows a partial sectional perspective view of the catheter of FIGS. 1A and 1B being used in accordance with a second embodiment of the method of the present invention;

FIG. 5 shows an embodiment of the invention including a second side or flush port.

DESCRIPTION

Figure 3A:
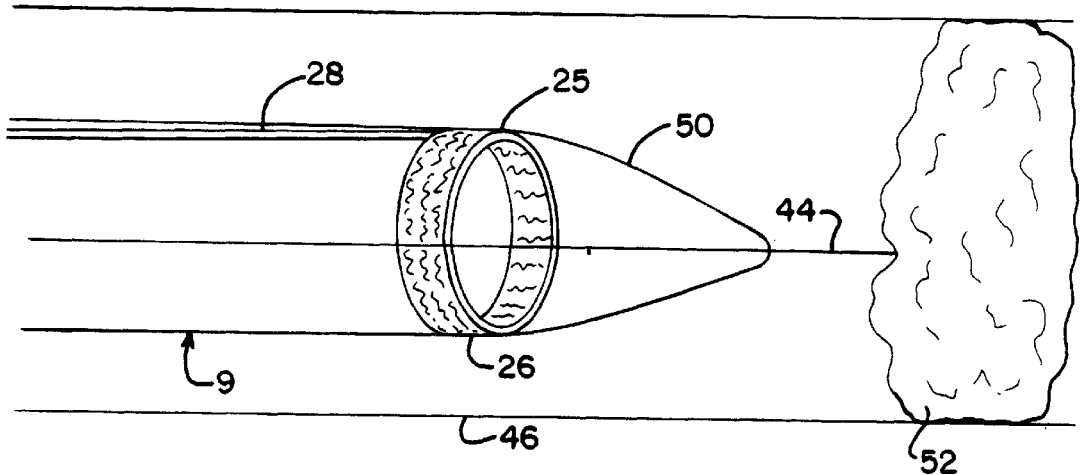
FIGS. 3A through 3E show partial sectional perspective views of the catheter of FIGS. 1A and 1B being used in accordance with an embodiment of the method of the present invention to remove a blood clot from a blood vessel.

Referring to FIGS. 1 and 2, a catheter that is an embodiment of the present invention is shown. It is to be understood that embodiments of the invention may take the form of a typical catheter, a guide catheter, an introducer sheath or the like. Catheter cylindrical body 9 features Luer Lock hub 10 mounted on its proximal end 11 and a central lumen 12 through which a guide wire and other devices may be passed. The proximal portion 21 of catheter body 9 is fixed so as to provide rigidity. Catheter body 9 is preferably constructed of either a plastic polymer or a metallic substance. At junction point 22, the catheter body 9 divides into flexible members 23 that, in their unexpanded state, as shown in FIG. 1A, maintain the same cylindrical shape as proximal portion 21 over the remaining length of the catheter body 9. The distal portion of catheter body 9 may involve as few as two and as many as eight flexible members 23. The flexible members 23 provide a measure of rigidity to the distal portion of the catheter body while at the same time allowing radial expansion.

Distal tip 25 (FIG. 3A) features an inflatable cuff 26 attached about the circumference of the interior surface of members 23. Cuff 26 may be attached by bonding using biologically inert adhesives or a loop formed in the material of the flexible members 23. Cuff 26 is preferably composed of a slightly elastic plastic polymer which is biologically inert and expands to a predictable degree under inflation pressure. Plastics such as polyurethane may be used for this purpose. The walls of inflatable cuff 26 are thin, so as to minimize added thickness to the profile of lumen 12.

A cuff inflation tube 28 provides a dedicated inflation lumen 29 that is in fluid communication with cuff 26. Cuff inflation tube 28 is connected to the interior surface of one of the members 23 so as to run longitudinally through lumen 12. A side port 30 is connected to the proximal portion 21 of catheter body 9 and communicates with the proximal end of cuff inflation tube 28. A syringe 32 connects to side port 30 via a Luer Lock hub 34. Inflation of cuff 26 is accomplished by the injection of fluid, most appropriately one containing a radiopaque contrast, through cuff inflation tube 28 via syringe 23. The inflation of cuff 26 with liquid containing radiopaque contrast allows for easier positioning of the catheter during an interventional radiological procedure.

In FIGS. 1B and 2B, catheter body 9 is shown with the distal end of the lumen opening 35 in an expanded state. The diameter of expanded opening 35 is chosen depending upon the size of the tubular structure of the human body within which the catheter is placed. Opening 35 may be expanded with the intent of engaging the interior of the wall of the tubular structure so as to create a circumferential occlusive seal therein. However, in situations in which flow through the tubular structure cannot be completely interrupted, as, for example, in a main artery, the expanded diameter may be chosen so as to create an enlarged orifice, but without circumferential contact with the interior of the wall of the tubular structure. Flow may then continue around opening 35.

As shown in FIGS. 2A and 2B, encircling the entirety of catheter body 9 is an elastomeric membrane sleeve 40 (omitted for clarity in FIGS. 1A and 1B), affixed to the outer surface of the catheter body members 23. The elastomeric membrane sleeve 40 serves two main purposes. First, the membrane, by its elastic nature, contracts the members 23 so that the distal portion of catheter body 9 resumes its original shape after cuff 26 has been deflated. Secondly, since inflation of cuff 26 forces the flexible members 23 away from one another, thus creating substantial space between them, the ability of the catheter to accept and trap material is compromised in the absence of a membrane which spans these members. Elastic membrane sleeve 40 thus maintains a continuous wall about lumen 12 through which material drawn thereinto may pass to the exit port 42.

FIGS. 3A through 3E show the catheter being used in accordance with the method of the invention to remove a blood clot from a vessel. It is to be understood that use of the device in a blood vessel to remove a blood clot is presented as an example only and that the catheter and method of the present invention may be used to remove a variety of undesirable materials from a number of different tubular structures in the human body. The latter includes, but is not limited to, tubular structures of the biliary, excretory and vascular systems.

Figure 3B:
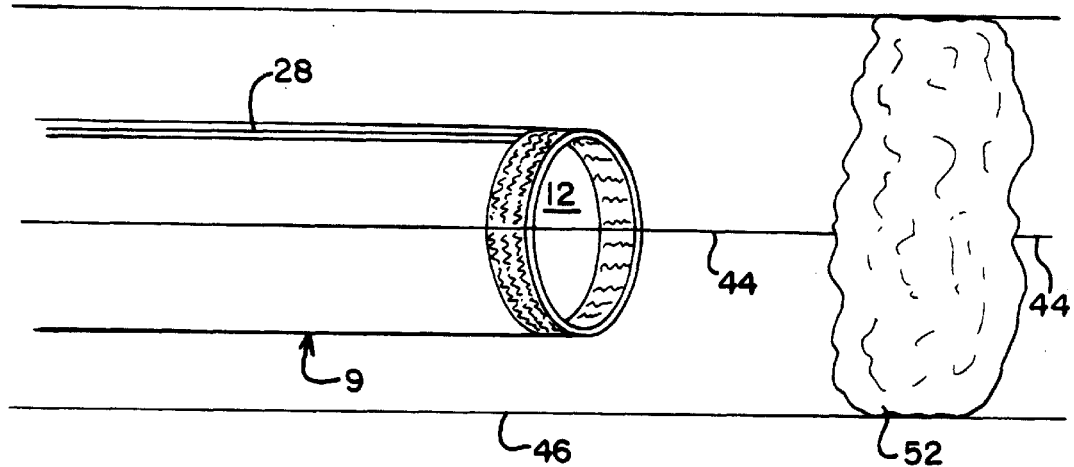

As shown in FIG. 3A, a guide wire 44 has been inserted into the blood vessel 46. Next, catheter body 9 is introduced into blood vessel 46 with a central dilator 50 disposed ahead of the catheter. This is done so that the blunt distal tip 25 of the catheter body 9 does not damage the walls of vessel 46 as it is advanced. During this stage, cuff 26 is deflated. Catheter body 9 is guided to the location of a blood clot 52 via travel along guide wire 44 (which, it is noted, passes through the clot). Once the catheter body 9 is in the proper position, as shown in FIG. 3B, central dilator 50 is removed. At this point, catheter body 9 may be partially withdrawn if desired. However, it should never be advanced without central dilator 50 in place for the reason mentioned above.

Figure 3C:
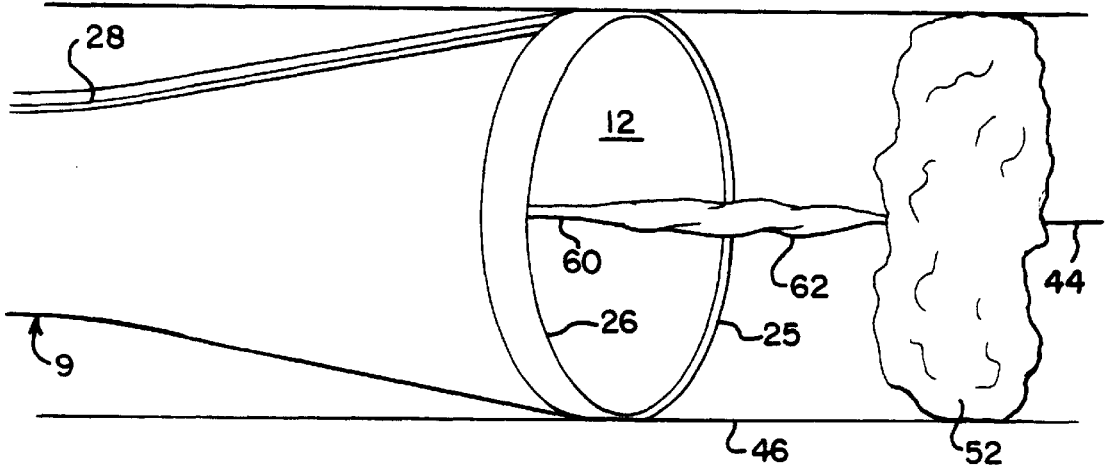

Next, as shown in FIG. 3C, cuff 26 is inflated so that the distal tip 25 of catheter body 9 is able to accommodate clot 52. A balloon catheter 60 is then passed, in a deflated condition, along guide wire 44, through lumen 12 and through clot 52. Such balloon catheters are well known in the art.

Figure 3D:
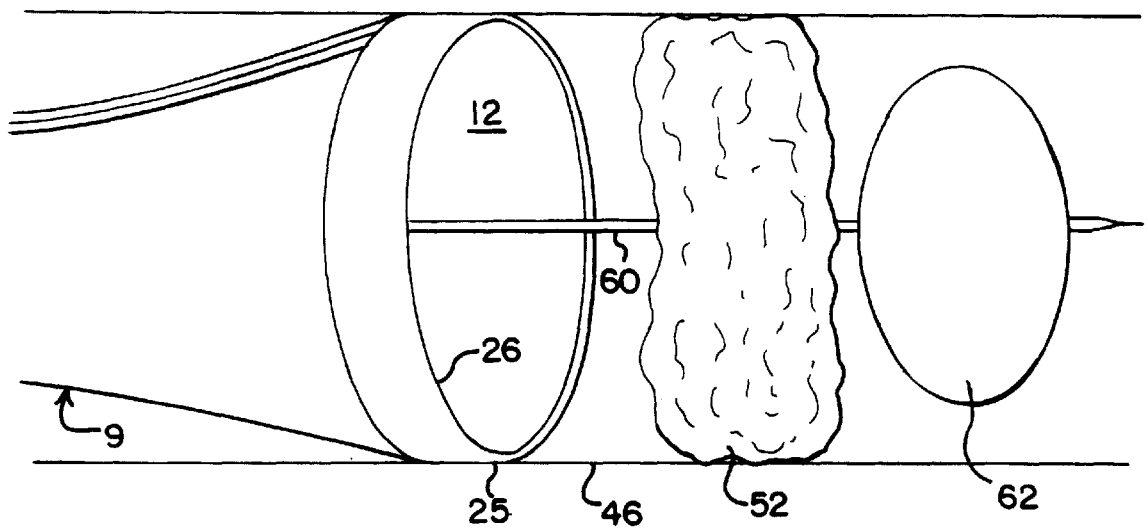
Figure 3E:
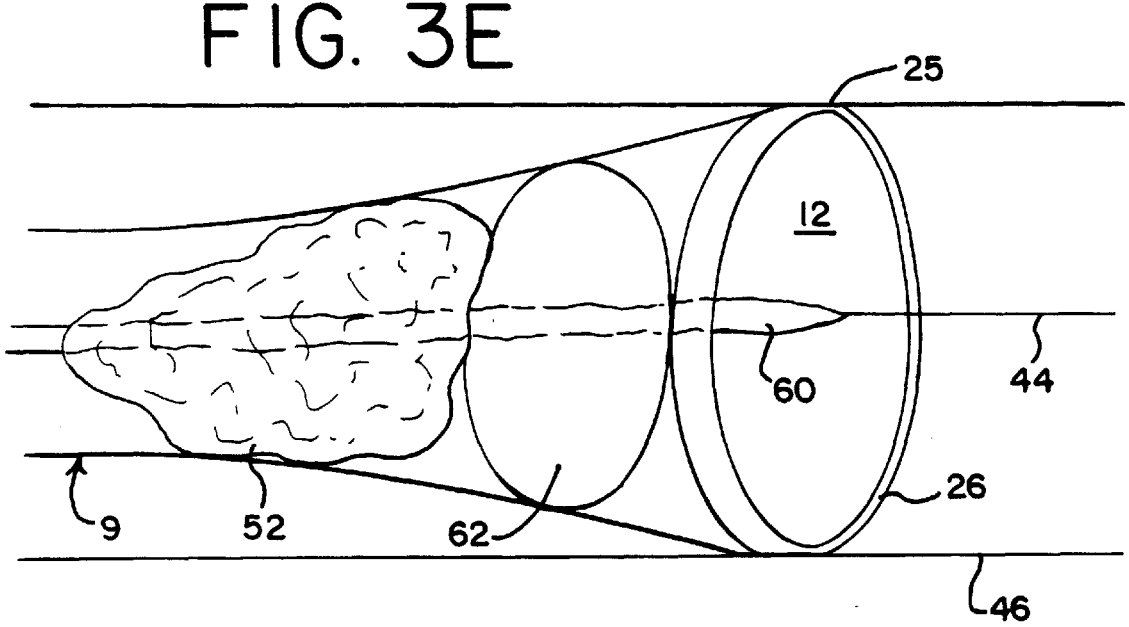

Referring to FIG. 3D, once the balloon portion 62 of balloon catheter 60 has passed through clot 52, it is inflated via methods well known in the art. After the balloon portion 62 is inflated, as shown in FIG. 3E, the clot is pulled into catheter body 9 with expanded distal tip 25 providing proper clearance. With clot 52 captured within catheter body 9, cuff 26 is deflated so that the distal tip 25 contracts back towards its original size and shape. This results in clot 52 being compacted by the interior surfaces of members 23 as they are pulled radially inwards by elastomeric membrane sleeve 40. During this stage, the balloon portion 62 of balloon catheter 60 is also permitted to deflate. With distal tip 25 contracted back to approximately its original size and shape, and clot 52 compacted within the catheter body 9, the unit may be easily removed from the vessel of the patient. Alternatively, the balloon catheter 60 may be used to pull clot 52 through the remaining portion of catheter body 9, including proximal end 21, through lumen 12 and out exit port 42 (see FIGS. 1A and 1B). In this manner, clots are removed from the vessel and body without necessitating reinsertion of catheter body 9 should retrieval of additional clots be desirable.

While a balloon catheter 60 has been used in the example presented in FIGS. 3A through 3E, a snare or other elongated tool may be used as an alternative. This would be necessary, for example, in situations wherein the undesirable material to be removed is not penetrable. Furthermore, the elongated tool could be inserted into the blood vessel through a supplemental puncture site (illustrated in phantom at 96 in FIG. 4) separate from that of the catheter and distal to the clot 52.

As stated previously, the distal opening 35 of the lumen may be sized and expanded so that a circumferential occlusive seal, illustrated in phantom at 100 in FIG. 4, is formed between the distal tip 25 of the catheter and the blood vessel 46. As a result, the blood flow, flowing in the direction illustrated by arrow 102 in FIG. 4, is interrupted so that a reduction of pressure occurs in the vicinity of the distal tip 25 of the catheter 9. The resulting reversed pressure gradient causes the blood to temporarily flow towards the distal end of the catheter, as illustrated by arrow 103. In some instances, this reversed flow is strong enough that the clot 52 is propelled through the opening 35 and into the catheter. As a result, usage of a balloon catheter in the manner illustrated in FIGS. 3C–3E is not necessary or may only assist the flow in moving the material towards the catheter opening.

The approach of the above paragraph tends to work best when the blood flow in the direction of arrow 102 is at a higher rate and/or the clot 52 is smaller in size. With regard to the latter, a clot fragmentation device may be inserted either through the catheter lumen 12 or a supplemental puncture site 96 (FIG. 4) distal to the material and utilized to fragment material 52. Such clot fragmentation devices are known in the art.

As shown in FIG. 5, the proximal portion 21 of the catheter body 9 may be equipped with a second side arm or flush port 104 that may include a Luer Lock hub 105. Flush port 104 is in communication with the catheter lumen 12. After the guide wire is removed from the catheter lumen 12, medications or other fluids 106, including fluids to break up the material 52 (FIG. 4), may be injected through the flush port 104 and lumen 12 via syringe 108. Alternatively, the flow of blood towards the opening 35 may be enhanced by attaching a suction device, illustrated at 110 and in phantom at 112 in FIG. 5, to the flush port 104. More specifically, the physician may operate the suction device at his or her discretion to electively enhance the reversed pressure gradient in the blood vessel 46.

While the preferred embodiments of the invention have been shown and described, it will be apparent to those skilled in the art that changes and modifications may be made without departing from the spirit of the invention, the scope of which is defined by the appended claims.

What is claimed is:

1. A method for retrieving material from tubular structures within the human body comprising the steps of:
    a) inserting a guide wire into the tubular structure;
    b) guiding a catheter featuring an expandable lumen opening along the guide wire proximate to the material;
    c) expanding the lumen opening to a size sufficient to permit the material to be received in the lumen; and
    d) moving the material into the lumen opening.

2. The method of claim 1 further comprising the steps of:
    e) contracting the lumen opening; and
    f) removing the catheter from the tubular structure.

3. The method of claim 2 further comprising the step of attaching an inflatable cuff to the catheter in a position proximate to the expandable lumen opening and wherein the lumen opening is expanded in step c) by inflating the cuff and the lumen opening is contracted in step e) by deflating the cuff.

4. The method of claim 1 further comprising the steps of placing a central dilator through the catheter prior to step b) and removing the central dilator prior to step d).

5. The method of claim 1 wherein step d) includes the substeps of:
    i) deploying a balloon catheter through the lumen opening and past the material;
    ii) inflating the balloon catheter; and
    iii) drawing the material into the lumen opening by withdrawing the balloon catheter.

6. The method of claim 1 further comprising the step of attaching an inflatable cuff to the catheter in a position proximate to the expandable lumen opening and wherein the lumen opening is expanded in step c) by inflating the cuff.

7. The method of claim 1 further comprising the step of pulling the material out of the catheter through an exit port external to the tubular structure.

8. The method of claim 1 wherein step d) includes the substeps of:
   i) puncturing the tubular structure distal to the material to create a supplemental puncture site;
   ii) inserting an elongated tool through the supplemental puncture site; and
   iii) pushing the material towards lumen opening.

9. The method of claim 1 further comprising the step of fragmenting the material prior to step d).

10. The method of claim 9 wherein the material is fragmented by inserting a clot fragmentation device through the lumen opening of the catheter and moving it to the material.

11. The method of claim 9 wherein the step of fragmenting the material includes the substeps of:
    i) puncturing the tubular structure distal to the material to create a supplemental puncture site;
    ii) inserting a clot fragmentation device through the supplemental puncture site; and
    iii) moving the clot fragmentation device to the material.

12. The method of claim 1 further comprising the steps of removing the guide wire from the tubular structure after step b) and injecting a fluid through the lumen opening into the tubular structure.

13. A method for retrieving material from tubular structures within the human body comprising the steps of:
    a) inserting a guide wire into the tubular structure;
    b) guiding a catheter featuring a tip with an expandable lumen opening along the guide wire to a position proximate to the material;
    c) expanding the lumen opening so that a circumferential occlusive seal is formed between the catheter tip and an inner surface of the tubular structure; and
    d) receiving the material in the lumen opening due at least in part to a reversed flow in the tubular structure proximate to the catheter tip as a result of step c).

14. The method of claim 13 further comprising the steps' of:
    e) contracting the lumen opening; and
    f) removing the catheter from the tubular structure.

15. The method of claim 14 further comprising the step of attaching an inflatable cuff to the catheter in a position proximate to the expandable lumen opening and wherein the lumen opening is expanded in step c) by inflating the cuff and the lumen opening is contracted in step e) by deflating the cuff.

16. The method of claim 13 further comprising the step of applying suction to a catheter port external to the tubular structure after step c) to enhance the reversed flow of step d).

17. The method of claim 13 further comprising the steps of placing a central dilator through the catheter prior to step b) and removing the central dilator prior to step d).

18. The method of claim 13 further comprising the step of attaching an inflatable cuff to the catheter in a position proximate to the expandable lumen opening and wherein the lumen opening is expanded in step c) by inflating the cuff.

19. The method of claim 13 further comprising the step of pulling the material out of the catheter through an exit port external to the tubular structure.

20. The method of claim 13 wherein step d) includes the substeps of:
    i) puncturing the tubular structure distal to the material to create a supplemental puncture site;
    ii) inserting an elongated tool through the supplemental puncture site; and
    iii) pushing the material towards lumen opening.

21. The method of claim 13 further comprising the step of fragmenting the material prior to step d).

22. The method of claim 21 wherein the material is fragmented by inserting a clot fragmentation device through the lumen opening of the catheter and moving it to the material.

23. The method of claim 21 wherein the step of fragmenting the material includes the substeps of:
    i) puncturing the tubular structure distal to the material to create a supplemental puncture site;
    ii) inserting a clot fragmentation device through the supplemental puncture site; and
    iii) moving the clot fragmentation device to the material.

24. The method of claim 13 further comprising the steps of removing the guide wire from the tubular structure after step b) and injecting a fluid through the lumen opening into the tubular structure.

* * * * *